United States Patent [19]

Vaguine

[11] 4,446,874
[45] May 8, 1984

[54] MICROWAVE APPLICATOR WITH DISCOUPLED INPUT COUPLING AND FREQUENCY TUNING FUNCTIONS

[75] Inventor: Victor A. Vaguine, Dallas, Tex.

[73] Assignee: Clini-Therm Corporation, Dallas, Tex.

[21] Appl. No.: 335,631

[22] Filed: Dec. 30, 1981

[51] Int. Cl.³ .............................................. A61N 5/02
[52] U.S. Cl. ............................... 128/804; 219/10.55 F
[58] Field of Search ................. 128/804; 219/10.55 R, 219/10.55 A, 10.55 F

[56] References Cited

U.S. PATENT DOCUMENTS

| | | | |
|---|---|---|---|
| 2,407,690 | 9/1946 | Southworth | 128/804 X |
| 3,065,752 | 11/1962 | Potzl | 128/422 |
| 4,108,147 | 8/1978 | Kantor | 128/804 |
| 4,282,887 | 8/1981 | Sterzer | 128/804 |
| 4,341,227 | 7/1982 | Turner | 128/804 |

FOREIGN PATENT DOCUMENTS

| | | | |
|---|---|---|---|
| 36040 | 9/1981 | European Pat. Off. | 128/804 |
| 748828 | 7/1933 | France | 128/804 |

OTHER PUBLICATIONS

McEuen et al., "Temp. Controlled Cavity Applicator . . .", Symp. Elec. Fields Bio. Systems, Canada, Jun. 1978, pp. 113-121.

Primary Examiner—Lee S. Cohen
Attorney, Agent, or Firm—Richards, Harris & Medlock

[57] ABSTRACT

An improved microwave applicator includes a frequency tuner discoupled from an input power coupling tuner. The frequency tuner includes parallel elongated dielectric bars axially adjustable in a dielectric-filled waveguide. A central passageway space is provided between the dielectric bars for incorporation of an input coupling tuner in the form of a magnetic loop assembly. The magnetic loop assembly includes a metal loop connected to a metal block and means for axially adjusting the position of the loop assembly within the central passageway space between the elongated dielectric members. Frequency and input coupling tuning controls, as well as the microwave input connector, are located behind the closed end of the waveguide applicator to facilitate optimization of mutual positioning of multiple applicators.

44 Claims, 7 Drawing Figures

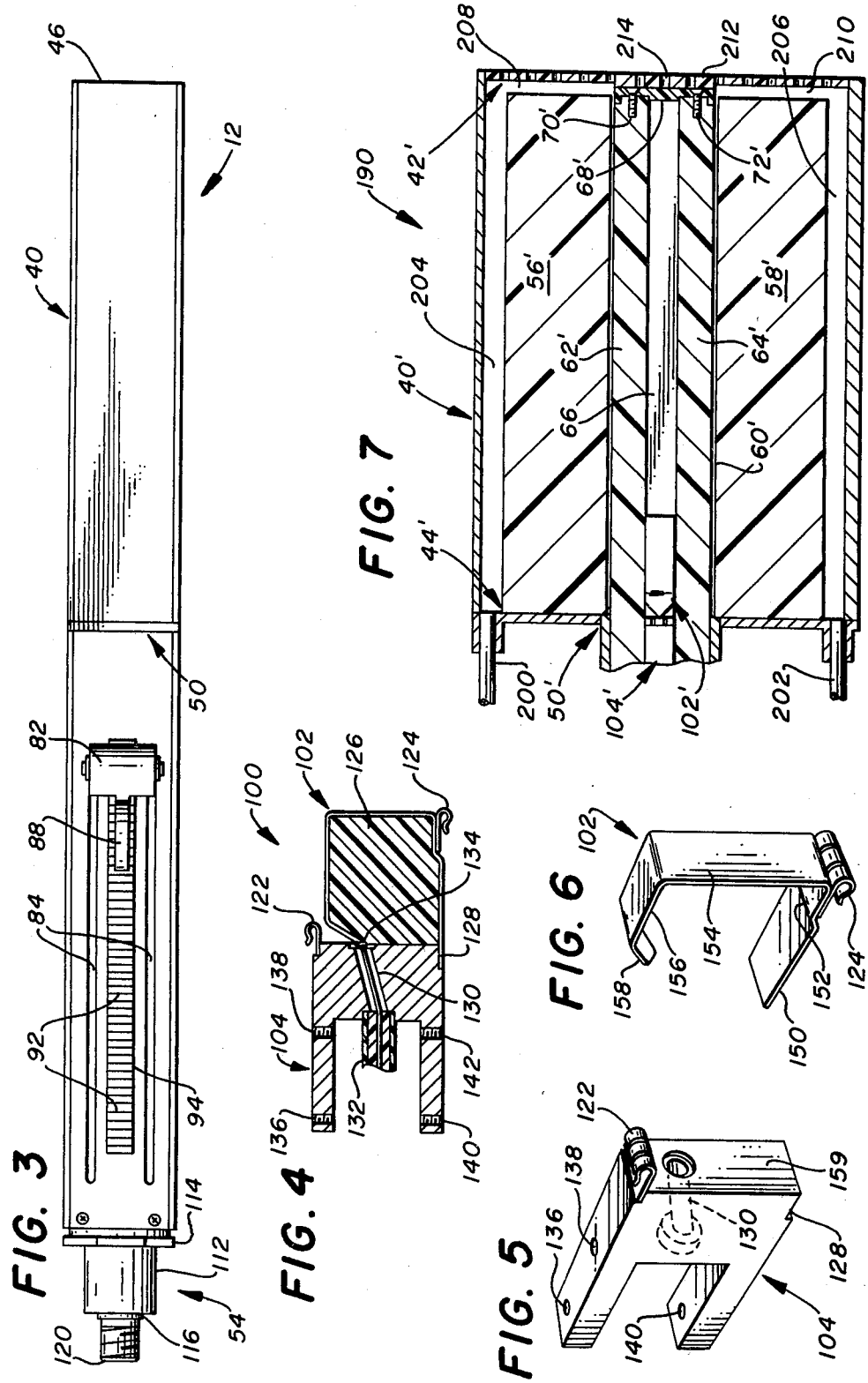

MICROWAVE APPLICATOR WITH DISCOUPLED INPUT COUPLING AND FREQUENCY TUNING FUNCTIONS

TECHNICAL FIELD

This invention relates to a microwave applicator having improved frequency and input power coupling tuning capabilities and more particularly to a microwave applicator having discoupled frequency and input coupling tuning functions.

BACKGROUND ART

Hyperthermia is the heating of living tissue for therapeutic purposes. Hyperthermia has been used as a method of treating cancer by means of raising the temperature of a tumor locally, or a region of the body in which the tumor is located, or of the whole body. It has long been known that high heat can trigger the natural regression and/or remission of tumors. Because of its effect on cancer cells, hyperthermia may be used as an independent therapy or in conjunction with other cancer therapies, such as radiation, surgery, chemotherapy, and immunotherapy to enhance the effectiveness of these therapeutic modalities. Current hyperthermia techniques used in cancer therapy include regional perfusion with heated fluids, microwave heating, fluid emersion, low frequency (RF) current fields, and ultrasound.

Three of the most common types of currently used hyperthermia techniques involve radio frequency, microwaves and ultrasound. Radio frequency and microwave equipment may be used for local, regional and whole body heating. Ultrasound can also be used for local and regional heating.

Microwave hyperthermia systems have been developed utilizing direct contact microwave waveguide applicators. The depth of penetration of the microwave energy is frequency-dependent and the penetration is also a function of tissue, anatomical structure and blood flow dynamics. The design of the microwave waveguide applicator has direct impact on the thermal patterns in human body tissue. In addition, sharp changes in patient contour within the heated area, as in the head and neck region, will have an influence on the thermal distribution. In some microwave hyperthermia treatment systems microwave power from a microwave generator can be transmitted to the load (human tissue) through a direct contact microwave applicator. Such microwave hyperthermia treatment systems further include control instrumentation. A frequency counter may be connected to a directional coupler for microwave frequency measurements. A power meter may be connected to a forward power port of a dual directional coupler for forward power measurements. A power meter may also be connected to a reflected power port of a dual directional coupler for reflected power measurements from a microwave applicator. In order to obtain a good efficiency of microwave energy transmission from a microwave energy generator to human tissue, reflected microwave power from the load should be minimized. Reflected microwave energy from the load may be minimized by tuning the frequency of the applicator and/or tuning the coupling of the microwave power to the applicator.

Prior art microwave direct contact applicators have been designed at only single or dual operating frequencies. These applicators can be adjusted within only a very narrow frequency range with a tuning device of some kind. Microwave input power coupling is typically used, such as either an adjustable or fixed antenna stub. The antenna stub is a part of applicator design and is installed in a region of maximum electric field which is located at one quarter waveguide wavelength from the closed end of the applicator along the applicator axis. Since the position of the maximum electric field changes rapidly with frequency, a required input coupling is provided only within a narrow frequency range at the design frequency. The second frequency is usually of an arbitrary value. In typical hyperthermia systems of the prior art, the microwave applicator had an adjustable antenna stub installed in a region of maximum electric field at one quarter waveguide wavelength from the closed end of the applicator along the applicator axis. A tuning device operated to adjust the frequency within a very narrow frequency range. The microwave applicator was designed only for a single operating frequency with very narrow frequency adjustments provided by the tuning device. In some cases, a second operating frequency of arbitrary value could be obtained. A typical prior art cylindrical waveguide direct contact microwave applicator of present systems operates at a frequency of 433 MHz. Since the position of the maximum electric field changes rapidly with changes in frequency, the required input coupling is provided only within a very narrow frequency range of the design frequency.

Microwave applicators have been developed which have attachments on the top, bottom, or sidewalls for making tuning adjustments for the applicator. The placement of such attachments have proven to be undesirable in multiple applicator configurations in which the applicators are positioned closely to each other in an array with varying angles of separation between adjacent applicators to optimize the heating pattern in the treatment area.

Microwave applicators have been used with various cooling systems to reduce the heat produced by the applicator at the surface of the treatment area. Water cooling belts have been located between the applicator and the surface treatment area to circulate cool water through the belt to carry off some of the surface heat. Cool air has also been forced by blowers in the space between the face of the microwave applicator and the surface of the treatment area.

A need has thus arisen for a microwave applicator having discoupled frequency and input power coupling tuning over a broad range to provide microwave matching over a broad range of microwave loads in a clinical environment, including multiple applicator modality, which usually involves microwave interaction among applicators, especially incoherent modality of operation. A need has also arisen for having all the tuning functions, including RF connectors, located behind the closed end of the applicator in the applicator's cross sectional geometry for facilitating the arrangement of an array of applicators. A need has also arisen for operating a microwave applicator in a direct or indirect contact mode of operation, where the input power coupling is adjustable over a broad range of clinical microwave load conditions. A need has also arisen to reproduce a microwave applicator input coupling and frequency tuning setting for a prescribed course of clinical treatment, especially for operation of multiple microwave applicators.

SUMMARY OF THE INVENTION

The microwave applicator of the present invention separates the frequency and input coupling tuning functions. Effective frequency tuning of the applicator is achieved by inserting or removing from the applicator dielectric material with a high dielectric constant. Greater sensitivity and greater frequency tuning range can be achieved by positioning the dielectric tuning material in the center of the applicator where there is maximum electric field strength for the $TE_{01}$ fundamental mode.

In the preferred embodiment, a broad range of frequency tuning for the applicator is achieved through moving two dielectric bars spaced 0.5 inches apart along the central axis of the applicator, where the dielectric bars are removed from or added into the cavity of the applicator. The dielectric bars can be removed into an appendix, a rectangular metal sleeve, extending from the back wall of the applicator through two small apertures in the back wall. The cross section of the metal extension is sufficiently small so that the next microwave modes $TE_{02}$ cannot be excited in the extension and no energy propagates from the applicator to the extension.

The range of frequency tuning is ±10% of the applicator's central frequency. The frequency tuning control enables the applicator to be tuned for minimum reflected power, preferably less than five percent of the forward power. The frequency adjustment is calibrated to reproduce frequency tuning settings in the course of a prescribed clinical treatment.

The tuning of the microwave power input coupling of the microwave signal to the applicator is discoupled from the frequency tuning. Input power coupling is achieved by positioning a metal loop along the central axis of the applicator in the location of maximum magnetic field intensity, which is in immediate proximity to the back wall of the applicator. In the preferred embodiment, an open metal loop filled with a dielectric material is attached to a metal block which provides a bridge for current flowing across the appendix in the closed end for the $TE_{01}$ mode. The metal loop and metal block are adjustable along the central axis within the passageway between the two dielectric frequency tuning bars. As compared to the antenna stub the proposed input coupling design requires only one mechanical motion to achieve variable input power coupling.

A coaxial cable from a microwave power generator is fed through an opening in the metal block, and the inner conductor is connected to the end of the metal loop. The outer conductor is connected to the metal block. Finger contacts are attached to the metal loop and metal block for providing microwave contact on both internal sides of the waveguide. The metal block is connected to a threaded rod and is connected to a calibrated tuning block. The tuning block allows for adjustment and calibration of the input power coupling. A broad range of coupling tuning capability enables the applicator to be used in the direct contact or indirect contact mode of operation, as well as to tune the applicator for minimum reflected power, preferably less than five percent of forward power, for a variety of microwave lead conditions, pertinent to clinical requirements.

Another aspect of the present invention is the location of all tuning functions and microwave power connections directly behind the applicator and within the cross sectional geometry of the applicator. The microwave applicator is free from any control mechanisms or other attachments on the top, bottom or side, enabling it to be arranged in a multiple applicator configuration with any desired angle of separation between applicators, including zero degree of separation.

In yet another aspect of the present invention, passageway channels are provided through the dielectric material filling the microwave applicator for directing and circulating cooled air through a set of small holes in a dielectric front cover of the applicator. The inlet openings for connection of the cooled air source are provided behind the back wall of the microwave applicator to maintain the top, bottom and side walls free from any attachments as required for multiple applicator operation modality.

DESCRIPTION OF DRAWINGS

For a more complete understanding of the present invention and the advantages and features thereof, reference is now made to the accompanying Detailed Description taken in conjunction with the following figures in which:

FIG. 3 is a plan view of the microwave applicator of FIG. 2;

FIG. 4 is a cross sectional view of the magnetic coupling loop assembly of the microwave applicator of FIG. 2;

FIG. 5 is a perspective view of the metal tuning block of the magnetic coupling assembly;

FIG. 6 is a perspective view of the metal loop of the magnetic coupling assembly; and FIG. 7 is a partially cut away cross sectional view of the microwave applicator of FIG. 1 with passageway channels for air cooling.

DETAILED DESCRIPTION

Figure 1:
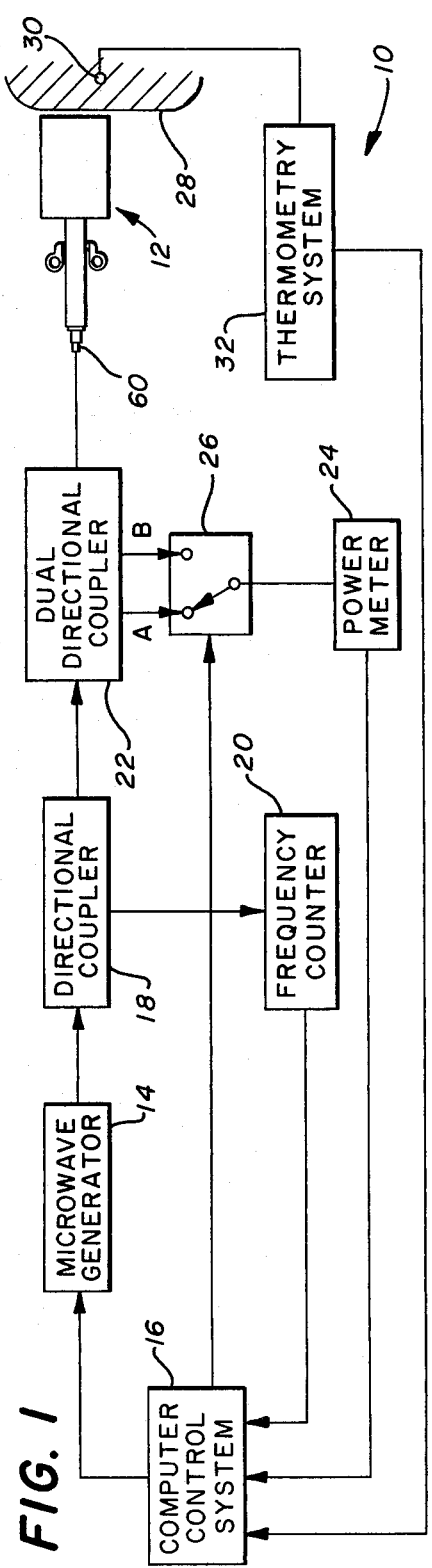
FIG. 1 is a block diagram drawing of a microwave hyperthermia system utilizing the microwave applicator of the present invention.

FIG. 1 illustrates a hyperthermia treatment system, generally identified by the reference numeral 10, including a microwave applicator of the present invention, generally identified by the reference numeral 12.

A microwave generator 14 is the source of microwave power for the system 10. The output power of the microwave generator 14 is controlled by a computer control system 16. The output power from the microwave generator 14 is fed through a directional coupler 18, which is connected to a frequency counter 20 for frequency measurements. The output power of the microwave generator 14 is fed to the microwave applicator 12 via the directional coupler 18 and a dual directional coupler 22.

A power meter 24 and power meter coaxial switch 26 provide a means for measurements of the forward and reflected power. The power meter switch 26 is shown connected to the forward power port A of the dual directional coupler 22 for measurements of forward power. The power meter switch 26 may be connected to the reflected power port B of the dual directional coupler 22 for measurements of the reflected power. The output of the frequency counter 20 and power meter 24 is fed back to the computer control system 16. The computer control system 16 is also connected to control the coaxial switch 26. The microwave applicator 12 is shown in a direct contact with a treatment area of human tissue 28. A temperature sensor 30 is inserted into the treatment area 28, and a thermometry system 32 processes the temperature information from the sensor 30 and feeds it to the computer control system 16 for processing. Of course, more than one temperature sensor 30 may be used, including sensors located in a tumor or around the site of a tumor to develop the necessary temperature profile for a prescribed treatment. In addition, multiple applicators 12 may be positioned to conform to the treatment area contour. The applicators 12 may be positioned with adjoining open ends with any angle of separation, including zero angle of separation between the applicators.

The system shown in FIG. 1 operates as a closed loop. Feedback signals from temperature sensor(s) 30 through the thermometry system 32, signals from the frequency counter 20 and signals from the power meter 24 are fed into the computer control system 16 through a computer interface. Based on these feedback signals the computer 16 controls the output power of the microwave generator 14 and activates power meter coaxial switch 26 in required position A or B.

Figure 2:
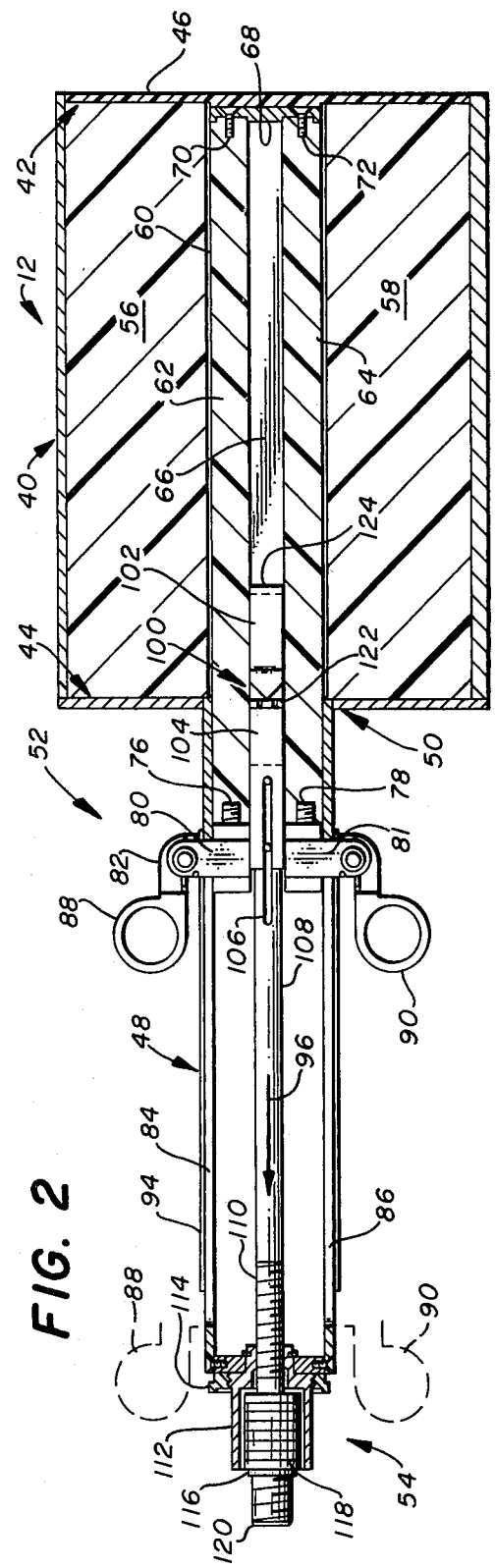
FIG. 2 is a cross sectional view of the microwave applicator of the present invention.

FIGS. 2 and 3 illustrate the preferred embodiment of the microwave applicator 12 of the present invention. The microwave applicator 12 includes a hollow rectangular waveguide applicator 40 having an open end 42 and a closed end 44. Microwave energy propagates in the rectangular waveguide 40 from the closed end 44 to the open end 42. The opened end 42 is covered by a very thin front plate 46 made from a clinically acceptable dielectric material, such as Teflon. An appendix 48, an elongated metal sleeve with a rectangular cross section, extends from a central aperture 50 in the closed end 44 of the waveguide 40. The central aperture 50 is sufficiently small in cross sectional area that both $TE_{01}$ and $TE_{02}$ modes cannot be excited in the appendix 48 and practically no microwave energy propogates from waveguide 40 into the appendix 48. The appendix 48 supports a frequency tuning control 52 and an input coupling tuning control 54.

The rectangular waveguide 40 is operated in the $TE_{01}$ mode. The $TE_{01}$ mode is the fundamental microwave mode of excitement in rectangular waveguides and has the lowest cutoff frequency as compared with other modes such as $TE_{02}$. The waveguide 40 cannot transmit below the cutoff frequency. A cylindrical waveguide applicator is also feasible for the present invention, where the applicator would operate in its fundamental mode, the $TE_{11}$ mode.

The rectangular waveguide 40 is filled with first and second dielectric slabs 56 and 58, providing a central passageway 60 extending from the central opening 50 in the closed end 44 to the dielectric face plate 46. The dielectric slabs 56 and 58 may be constructed from a low loss dielectric material, a suitable dielectric material may be used having a high dielectric constant (K) equal to thirty. The frequency tuning control 52 includes a pair of spaced and mechanically connected dielectric bars 62 and 64, providing a central passageway space 66 therebetween. In one embodiment, the dielectric bars 62 and 64 are spaced 0.5 inches apart. The elongated dielectric bars 62 and 64 are illustrated in FIG. 2 fully inserted within the central passageway 60 to obtain a minimum frequency setting. A spacing bar 68 made from a dielectric material, such as Teflon, is attached to the front end of the dielectric bars 62 and 64 by a pair of screws 70 and 72 made from a dielectric material, such as nylon.

The dielectric bars 62 and 64 extend in the opposite direction to a threaded manner 76, which is attached to a pair of transverse connecting arms 80 and a threaded member 78, which is connected to a pair of transverse connecting arms 81. The transverse connecting arms 80 and 81 are in turn connected to upper and lower spring loaded clamps 88 and 90, which may travel along a pair of top slots 84 and a pair of lower slots 86 formed in the appendix 48. The upper clamp 88 may be moved along the upper slot 84 so the teeth of the clamp engage one of the regularly spaced notches 92. The spaced notches 92 may be used as a calibrated frequency tuning scale 94. The scale 94 may be marked with suitable indicia, such as numbers or letters, to provide an operator with means for reproducing the frequency tuning adjustment for a patient over the course of repeated clinical treatment.

The frequency tuning control 52 as illustrated in FIG. 2, with the elongated dielectric bars 62 and 64 fully inserted, is adjusted in the minimum frequency position. The frequency tuning control 52 may be moved in the direction indicated by the arrow 96 for tuning the microwave applicator 12 for increasing frequencies. The tuning range of the microwave applicator 12 extends from a minimum frequency tuning position with the elongated dielectric bars 62 and 64 fully inserted and extends to a maximum frequency position with the elongated dielectric bars retracted in the position illustrated in phantom in FIG. 2. The frequency tuning control 52 provides a broad frequency tuning range. For example, a microwave applicator 12 may be tuned for operation at a particular selected frequency band, such as the 300 MHz, 400 MHz, 500 MHz, 600 MHz or 700 MHz. Such applicators could be tuned within selected frequency band, e.g., at least ±10% of the selected central frequency of the band.

The central passageway 66 between the elongated spaced dielectric bars 62 and 64 enables the input coupling loop assembly 100 to be position along the center of the waveguide 40. The input coupling loop assembly 100 is utilized in place of an adjustable RF antenna found in many existing microwave applicators in hyperthermia systems to improve the operation of the system. A metal loop 102 provides magnetic input power coupling, since the metal loop 102 is always located in the maximum magnetic field of the waveguide 40 for the fundamental mode independently of frequency. The fundamental mode of operation is the $TE_{01}$ mode for rectangular waveguides and the $TE_{11}$ mode for cylindrical waveguides. The metal loop 102 is positioned along the central axis of the waveguide 40 to prevent excitation of undesirable $TE_{02}$ modes and to excite the $TE_{01}$ mode by its location at maximum magnetic field intensity.

The metal loop 102 may be moved within the central passageway 66 along the center of the waveguide 40 for adjusting the input power coupling for a variety of clinical treatment situations. For example, the microwave applicator 12 may be operated in the indirect contact mode in which the input coupling loop assembly 100 would be adjusted for the variance in the load created by the air gap between the dielectric face plate 46 of the open end 42 of the waveguide 40 and the surface of the treatment area 28 of the patient (FIG. 1). In addition, the input coupling loop assembly 100 may be moved along the center of the waveguide 40 to fine tune the waveguide 40 for a clinical load, following the adjustment of the frequency tuning control 52. Generally, an efficient microwave hyperthermia system operates with reflected power less than five percent of forward power. The discoupled frequency tuning control 52 and input coupling control 54 can be adjusted separately to achieve optimal settings for a microwave hyperthermia system with reflected power less than five percent of forward power for a variety of clinical conditions. While the minimum reflected power condition is dependent on the particular clinical load, the frequency and coupling tuning controls 52 and 54 of the present invention have enabled an applicator 12 coupled to phantom models simulating actual clinical conditions with a variety of human tissue properties to be operated with reflected power less than one percent of forward power. In some instances, adjustments have been made to bring the microwave system to operate with reflected power less than one-tenth of one percent of forward power.

The metal loop 102 is connected to a metal block 104 which is in turn connected by an assembly 106 to a rod 108. The rod 108 is threaded at the opposite end 110 and is threaded into a coupling 112. The threaded coupling 112 is fitted within the open end of the appendix 48 by a support assembly 114. The end of the rod 108 extending through the threaded coupling 112 is affixed to a cylindrical adjustment mechanism 116. The adjustment mechanism 116 has graduated scales 118 for calibrating the coupling tuning adjustment. The rod 108 extends through the adjustment mechanism 116 to a coaxial cable connector 120. The cylindrical adjustment mechanism 116 may be rotated to move the metal loop 102 in or out of the central passageway 66 to provide a broad range of coupling tuning adjustment. The metal loop 102 is shown in FIG. 2 fully inserted for maximum coupling. The metal loop 102 may be partially removed from the cavity of the waveguide 40.

A first finger contact 122 is connected to the metal block 104 and a second finger contact 124 is connected to the metal loop 102 for engaging the sidewalls of the waveguide 40. The sidewalls of the waveguide 40 may be silver coated to ensure good electrical contact with the magnetic loop assembly 100. A dielectric material 126 fills the interior of the metal loop 102 as illustrated in FIG. 4.

FIG. 4 illustrates the input coupling loop assembly 100. The metal loop 102 is filled with a dielectric material 126 in order to provide dielectric material continuity in the proximity of back walls, and is connected to the metal block 104 at a point 128. The metal block 104 has an angular passageway 130 formed through it for receiving the coaxial cable 132. The outer conductor of the cable 132 is connected to the metal block 104, and the inner conductor of the coaxial cable 132 is soldered to the metal loop at the point 134. Finger contacts 122 and 124 provide means for connecting the loop assembly 100 to the sidewalls of the waveguide 40. Openings 136 and 138, 140 and 142 are formed along the upper and lower arms of the C-shaped metal block 104 to provide means for attachment to the assembly 106, illustrated in FIG. 2.

FIGS. 5 and 6 further illustrate the metal block 104 and metal loop 102, respectively. The metal loop 102 has elongated member 150 with a recessed section 152 for attaching the finger contact 124. The elongated member 150 is joined at right angles to an upright segment 154, the segment extending the furthest into the central passageway 66 of applicator 12. A segment 156 extends at right angles from segment 154 and extends to a downwardly projecting triangular section 158. Elongated member 150 is joined to the metal block 104, and the downwardly projecting section 158 is joined to the inner conductor of the coaxial cable 132. The forward surface 159 of the metal block 104 is the surface providing the current bridge between contacts 122 and 124.

FIG. 7 illustrates a microwave applicator 190 including a means for directing and circulating cooled air to the treatment area 28. Many of the component parts of the applicator 190 are substantially identical in construction and function to component parts of the applicator 12. Such component parts are designated in FIG. 7 with the same reference numerals utilized hereinabove in the description of the applicator 12, but are differentiated therefrom by means of a prime (') designation. In this embodiment, a pair of couplings 200 and 202 are attached to the closed end 44' of the waveguide 40' for connection to the source of cooled air (not illustrated). The air passageways 204 and 206 are provided along the direction of the central axis of the waveguide 40'. Air passageways 208 and 210 are connected to the passageways 204 and 206, respectively, and are parallel to the open end 42' of the waveguide 40'. A dielectric face plate 212 encloses the opening 42' of the applicator 40' and includes a plurality of openings 214 for directing cooled air to the treatment area 28 of the patient.

In operation, the clinical operator may select the size of the microwave applicator 12 having a operating frequency band, the frequency of operation, and the treatment temperature for the tumor, the temperature in the region of healthy tissue surrounding the tumor, the placement of temperature sensors and the duration of the treatment. As an example, the operator may select a microwave applicator 12 with an operating frequency band of 400 MHz to be operated at a frequency of 425 MHz to achieve the desired depth of penetration for a clinical treatment. The applicator 12 may be used in the direct contact mode of operation in which the dielectric face plate 46 is in contact with the treatment area 28, as illustrated in FIG. 1. Each microwave applicator has many frequency bands available.

The frequency tuning control 52 may be moved along the calibrated scale 94 to tune the microwave applicator 12 to match the load represented by the treatment area, the type of tissue and anatomical structure and blood perfusion conditions presented. The frequency tuning control 52 may be adjusted to obtain a minimum reflected power condition by inserting or removing the spaced dielectric bars 62 and 64 on the waveguide 40 and along its central axis. The reflected power reading may be obtained from the power meter 24. In one embodiment of a system utilizing the present invention, a series of lights may be utilized to indicate acceptable levels of reflected power. The frequency tuning control may be moved from a minimum position when the dielectric bars 62 and 64 are fully inserted to a maximum position when the bars are fully retracted. If the desirable reflected power condition cannot be met by frequency tuning control 52, the operator may adjust the input coupling control 54 to bring the reflected power within the desirable range.

The microwave applicator 12 may also be used in a clinical treatment for non-contact operation. There are certain clinical situations in which a patient is very sensitive to treatment area touched by applicators that the operationally more efficient direct contact method cannot be utilized. In such a clinical situation, the dielectric face plate 46 may be located a short distance from the treatment area, normally not greater than one inch. In laboratory operation using phantom models, a nearly linear relationship was observed between the position of the loop 102 and the gap between the face plate 46 and the treatment area 28. If treatment conditions indicate that the applicator 12 should be located three-quarters of an inch from the treatment area 28, then the adjustment mechanism 116 of the coupling control 54 may be rotated to retract the loop 102 three-quarters of an inch to retune the loop assembly 100 for that clinical load condition.

Although the preferred embodiments of the invention have been illustrated in the accompanying Drawings and described by the foregoing Detailed Description, it will be understood that the invention is not limited to the embodiments disclosed, but is capable of numerous rearrangements, modifications and substitutions of parts and elements without departing from the spirit of the invention.

I claim:

1. A microwave applicator for use in a microwave hyperthermia systems which includes a microwave generator for producing microwave electromagnetic energy and a means for determining the microwave power reflected from a treatment area, comprising:
  a hollow core metal waveguide having an open end and a closed end, whereby microwave electromagnetic energy is propagated in the direction from the closed end to the open end of said waveguide,
  input power coupling means for coupling said waveguide to the microwave generator of the hyperthermia system, said input power coupling means including means for tuning the coupling of said microwave electromagnetic energy from the microwave generator to said waveguide; and
  frequency tuning means for tuning the frequency of said waveguide, said frequency tuning means being discoupled from said means for tuning the coupling of said microwave electromagnetic energy, whereby the reflected power from the applictor is minimized by separately tuning said frequency tuning means and said means for tuning the coupling of said microwave electromagnetic energy.

2. The microwave applicator of claim 1 wherein said input power coupling means, said means for tuning and said frequency tuning means are located within the cross-sectional area of the closed end of said waveguide, whereby the clinical optimization of the mutual positioning of multiple applicators is facilitated including the positioning of adjacent applicators of the mutual applicator configuration with angles of separation including zero angle of separation.

3. The microwave applicator of claim 1, wherein said input power coupling means includes a metal loop positioned in the waveguide at a point of maximum field intensity for magnetically coupling said waveguide to the microwave generator.

4. The microwave applicator of claim 1, wherein said frequency tuning means comprises means for inserting or removing dielectric tuning material in said waveguide.

5. The microwave applicator of claim 4, wherein said dielectric tuning material inserted or removed from said waveguide is positioned in the center of said waveguide where there is maximum electric field strength for the $TE_{01}$ fundamental mode.

6. The microwave applicator of claim 5, wherein said dielectric tuning material is a pair of spaced apart dielectric bars extending along on opposite sides of the central axis of said waveguide, said spaced apart dielectric bars forming a central passageway for receiving said input power coupling means.

7. The microwave applicator of claim 4, further including an aperture formed in said closed end of said waveguide for passing said dielectric tuning material into or out of said waveguide.

8. The microwave applicator of claim 7 and further comprising:
  a metal appendix extending outwardly from said aperture away from said waveguide for receiving said dielectric tuning material inserted into or removed from said waveguide.

9. The microwave applicator of claim 4, wherein said dielectric tuning material has a high dielectric constant greater than 30.

10. The microwave applicator of claim 1 and further comprising:
  means for determining each of a plurality of settings for said frequency tuning means, whereby any of said settings may be reproduced for subsequent clinical treatments.

11. The microwave applicator of claim 1 and further comprising:
  means for determining each of a plurality of settings for said means for tuning the coupling of said microwave electromagnetic energy, whereby any of said settings may be reproduced for subsequent clinical treatment.

12. The microwave applicator of claim 1, wherein said waveguide has a rectangular cross section along the axis normal to the propagation of said microwave electromagnetic energy.

13. The microwave applicator of claim 12, wherein said rectangular waveguide is adapted to operate in the $TE_{01}$ mode.

14. The microwave applicator of claim 1, wherein said waveguide has a cylindrical cross section along the axis normal to the propagation of said microwave electromagnetic energy.

15. The microwave applicator of claim 14, wherein said cylindrical waveguide is adapted to operate in the $TE_{11}$ mode.

16. The microwave applicator of claim 1, wherein said waveguide is partially filled with a low loss dielectric material.

17. The microwave applicator of claim 11 and further comprising:
  at least one opening in said closed end of said waveguide for connecting said waveguide to a source of air; and
  air channel passageways formed through said dielectric material for directing air from said opening to said open end, whereby the treatment area is cooled by air circulating through said waveguide.

18. The microwave applicator of claim 17 and further comprising:
  a dielectric front plate covering the open end of said waveguide, said front plate including apertures formed therethrough for circulating cool air to the treatment area.

19. The microwave applicator of claim 1, further including:
  an aperture formed in said closed end of said waveguide, a metal appendix extending outwardly from said aperture on the opposite side of said closed end from said waveguide, and wherein said input power coupling means comprises:
a metal loop located along the central axis of the waveguide at a point of maximum magnetic field intensity;
means for removing a portion of said loop from said waveguide into said metal appendix
a metal block attached to one end of said metal loop, said block providing a current bridge across said appendix; and
finger contacts extending from said metal loop and said metal block for contacting the sidewalls of said waveguide and said metal appendix, whereby variable input power coupling tuning is achieved with a single mechanical adjustment regulating the portion of said loop within said cavity.

20. The microwave applicator of claim 16, wherein said metal loop is filled with a low loss dielectric material.

21. A microwave applicator for use in a microwave hyperthermia system which includes a microwave generator and means for determining the level of reflected power in relation to the forward power, comprising:
a dielectric-filled metal waveguide having an open end and a closed end, whereby microwave electromagnetic energy is propagated along the direction from the closed end of said waveguide to the open end;
a metal loop positioned in said waveguide at a point of maximum field intensity for magnetically coupling said waveguide to the microwave generator of the hyperthermia system,
an aperture in the closed end of said waveguide,
a metal appendix extending outward from said appendix opposite said waveguide,
means for removing a portion of said metal loop through said aperture for tuning the coupling of the waveguide to the microwave generator;
dielectric material located within said waveguide and moveable through said aperture; and
means for frequency tuning said waveguide by inserting or removing said dielectric material in said waveguide, said means for frequency tuning being independent of said means for removing, whereby input coupling adjustments provided by the positioning of said metal loop and frequency tuning adjustments provided by said means for frequency tuning may be made over a broad range of clinical load conditions.

22. The microwave applicator of claim 21 and further comprising:
means for determining the setting of said means for frequency tuning; and
means for determining the setting of said metal loop magnetically coupling said waveguide to the microwave generator, whereby tuning adjustments may be made to reproduce frequency tuning and coupling tuning settings for subsequent microwave hyperthermia clinical treatment.

23. The microwave applicator of claim 21, wherein said dielectric material comprises:
a pair of spaced apart dielectric bars extending along the central axis of said waveguide and forming a channel therebetween; and
said means for frequency tuning comprises:
means for inserting and removing said dielectric bars from said waveguide through said aperture, whereby said dielectric bars are axially adjustable along the central axis of said waveguide.

24. The microwave applicator of claim 21, wherein said waveguide has a rectangular cross section, said rectangular waveguide adapted to operate in the $TE_{01}$ mode.

25. The microwave applicator of claim 21, wherein said waveguide has a cylindrical cross section, said cylindrical waveguide adapted to operate in the $TE_{11}$ mode.

26. The microwave applicator of claim 21 and further comprising:
means for connecting a source of circulating cooled air through the closed end of said waveguide, and
air channel passageways formed through said dielectric material filling said waveguide, said passageways extending to the open end of said applicator for directing circulating cooled air through said applicator to the treatment area.

27. The microwave applicator of claim 26 and further comprising a thin dielectric front plate over the open end of said waveguide, said front plate including a plurality of apertures formed in said front plate and connected to said air channel passageways for directing cooled air to the treatment area.

28. A microwave applicator for use in a hyperthermia system which includes a microwave generator, comprising:
a hollow core metal waveguide having an open end and a closed end, whereby microwave electromagnetic energy is propagated in the direction from the closed end to the open end;
input power coupling means for coupling said waveguide to said microwave generator;
an aperture formed in the center of the closed end of said waveguide,
a metal appendix extending outside the waveguide from said aperture; and
means for inserting dielectric tuning material inside the waveguide or removing said dielectric tuning material from said waveguide through said aperture into said appendix, whereby frequency tuning adjustments are made by axially adjusting the position of said dielectric tuning material along the central axis of said waveguide where there is maximum electric field for the fundamental mode.

29. The microwave applicator of claim 28, wherein said wavguide is partially filled with a dielectric material, said dielectric material including a passageway formed for the insertion of said dielectric tuning material into said waveguide.

30. The microwave applicator of claim 28, and further comprising:
means for determining the axial settings of said dielectric tuning material inside said waveguide, whereby frequency tuning settings may be reproduced for repeated hyperthermia clinical treatments.

31. The microwave applicator of claim 28 wherein said input power coupling means is a metal loop located within said waveguide at the point of maximum magnetic field intensity.

32. The microwave applicator of claim 31, wherein said metal loop is positioned at the center of the closed end of said waveguide.

33. The microwave applicator of claim 32 further comprising:
means for axially adjusting the position of said metal loop within the waveguide, whereby the input coupling of said waveguide is tunable over a broad range of clinical load conditions.

34. The microwave applicator of claim 31, wherein said metal loop is filled with a dielectric material in order to provide dielectric material continuity in the proximity of the closed end of said waveguide.

35. The microwave applicator of claim 28, wherein said dielectric tuning material is a pair of elongated spaced apart dielectric bars having a channel formed therebetween and said input power coupling means further comprises:
a metal loop located in the channel between said dielectric bars, said metal loop being adapted for coupling to the microwave generator for magnetically coupling the generator to said waveguide; and
means for axially adjusting the position of said metal loop within the waveguide along the central axis of the channel, whereby the power coupling between said generator and said waveguide is tuned by positioning the metal loop along the central axis of the waveguide.

36. The microwave applicator of claim 35, wherein said metal loop and said dielectric bars are removable from said waveguide through said appendix.

37. The microwave applicator of claim 36 and further comprising:
means for determining the settings of said input power coupling means, whereby the settings of said input power coupling means may be reproduced for repeated microwave hyperthermia treatments.

38. The microwave applicator of claim 28, where said dielectric tuning material comprises:
elongated spaced apart dielectric bars; and
means for connecting the ends of said dielectric bars extending into said waveguide for controlling the spacing between said dielectric bars.

39. A microwave applicator for use in a microwave hyperthermia system which includes a microwave generator coupled to the applicator through a coaxial cable, comprising:
a hollow core metal waveguide having an open end and a closed end, whereby microwave electromagnetic energy is propagated in the direction from the closed end to the open end;
an aperture formed in the center of the closed end of said waveguide;
a metal appendix extending from said waveguide and encompassing said aperture;
a metal loop adapted for coupling to the microwave generator, said loop being positioned along the central axis of the applicator at a position of maximum magnetic field intensity for coupling said waveguide to the microwave generator;
means for retracting a portion of said metal loop into said metal appendix for tuning the power coupling between said microwave generator and said waveguide; and
means for providing a bridge for current flowing across the metal appendix for operating the microwave applicator in the $TE_{01}$ fundamental mode.

40. The microwave applicator of claim 39, wherein the cross sectional area of said metal appendix is smaller than that required for exiting said microwave electromagnetic energy in either of $TE_{01}$ or $TE_{02}$ modes.

41. The microwave applicator of claim 40 and further comprising:
means for frequency tuning said waveguide, said means for frequency tuning including means for inserting or removing dielectric material from said waveguide.

42. The microwave applicator of claim 41, wherein said dielectric material is inserted into and removed from said waveguide through said aperture into said metal appendix.

43. The microwave applicator of claim 42, wherein said dielectric material is a pair of spaced apart dielectric bars having a channel formed therebetween along the central axis of said waveguide, said channel providing an opening for receiving said means for retracting a portion of said metal loop into said appendix through said channel.

44. The microwave applicator of claim 39, wherein said means for providing a bridge for current comprises:
a metal block connected to said metal loop, said block being adapted for connection to one conductor of the microwave coaxial cable and said metal loop being adapted for connection to the other conductor of the coaxial cable; and
means for providing electrical contact between said metal loop and the metal walls of said waveguide and between said metal block and said metal appendix.

* * * * *

UNITED STATES PATENT AND TRADEMARK OFFICE
CERTIFICATE OF CORRECTION

PATENT NO. : 4,446,874
DATED : May 8, 1984
INVENTOR(S) : Victor A. Vaguine

It is certified that error appears in the above-identified patent and that said Letters Patent is hereby corrected as shown below:

Column 3, line 64, "lead" should be --load--.

Column 5, line 37, "propogates" should be --propagates--.
Column 6, line 2, "manner" should be --member--.
Column 9, line 22, "systems" should be --system--.
Column 9, line 40, "applictor" should be --applicator--.

Signed and Sealed this

Twelfth Day of March 1985

[SEAL]

Attest:

DONALD J. QUIGG

Attesting Officer    Acting Commissioner of Patents and Trademarks